(12) United States Patent
Deason (10) Patent No.: US 8,058,608 B1
(45) Date of Patent: Nov. 15, 2011

(54) DEVICE FOR IMAGING SCENES WITH VERY LARGE RANGES OF INTENSITY

(75) Inventor: Vance Albert Deason, Idaho Falls, ID (US)

(73) Assignee: The United States of America as represented by the Department of Energy, Washington, DC (US)

( * ) Notice: Subject to any disclaimer, the term of this patent is extended or adjusted under 35 U.S.C. 154(b) by 314 days.

(21) Appl. No.: 12/557,620

(22) Filed: Sep. 11, 2009

(51) Int. Cl.
*G02F 1/01* (2006.01)
(52) U.S. Cl. ............... 250/225; 250/201.1; 356/370; 356/491; 359/246; 359/251
(58) Field of Classification Search .......... 250/225, 250/207, 214 VT, 201.1; 356/313, 327, 370, 356/491; 359/246, 251, 301
See application file for complete search history.

(56) References Cited

U.S. PATENT DOCUMENTS

2010/0002923 A1 * 1/2010 Jiang et al. ............. 382/128

* cited by examiner

*Primary Examiner* — Kevin Pyo
(74) *Attorney, Agent, or Firm* — Michael J. Dobbs; Daniel D. Park; John T. Lucas (57) ABSTRACT

A device for imaging scenes with a very large range of intensity having a pair of polarizers, a primary lens, an attenuating mask, and an imaging device optically connected along an optical axis. Preferably, a secondary lens, positioned between the attenuating mask and the imaging device is used to focus light on the imaging device. The angle between the first polarization direction and the second polarization direction is adjustable.

16 Claims, 7 Drawing Sheets

DEVICE FOR IMAGING SCENES WITH VERY LARGE RANGES OF INTENSITY

GOVERNMENT INTERESTS

The United States Government has rights in this invention pursuant to Contract No. DE-AC07-05ID14517, between the U.S. Department of Energy (DOE) and Battelle Energy Alliance, LLC.

FIELD OF THE INVENTION

A high-dynamic-range imaging system, preferably used with large dynamic ranges of intensity, more preferably for imaging welding scenes.

BACKGROUND OF THE INVENTION

Various imaging devices, such as charge-coupled devices (CCD), charge-injection devices (CID), and complementary metal oxide semiconductor (CMOS) imaging devices have been extensively used for imaging scenes in many situations. In some situations, for example, when imaging welding scenes involving bright arcs and molten pools, imaging military activities having ammunition flashes or vehicle headlights, or imaging extra-solar planets having a vastly brighter parent star, the dynamic range of the intensity of light from the scenes can greatly exceed the dynamic range of the imaging device used.

To prevent the imaging device used from being partially or fully saturated, various methods have been used to attenuate the intensity and thereby increase the contrast of the bright areas of the scenes. Such methods comprise shuttering or filtering which globally reduce the intensity of light from the scenes, irrespective of bright areas or dimmer areas of the scenes.

Shuttering is a method for reducing light globally by reducing the exposure time of the imaging devices to the light from the scenes. By mechanically shuttering the light from the scenes to the imaging devices periodically, or by electronically discharging the imaging devices periodically, shuttering globally reduces the total amount of light. Filtering also globally reduces light from the scenes by attenuating light using one or more filters.

Another method of preventing the imaging device from being partially or fully saturated is high intensity light illumination. In high intensity light illumination, dimmer areas of the scenes are illuminated using flashlamps or lasers to provide a more uniform illumination throughout the scene. Shuttering synchronized with the external illumination or other global means of intensity reduction can then be used to bring the dynamic range of the entire scenes into conformity with the dynamic range of the imaging device. However, high intensity light illumination requires high energy consumption. Furthermore, in some situations, for example, imaging extra-solar planets having a vastly brighter parent star, the scenes to be imaged cannot be illuminated using flashlamps or lasers.

SUMMARY OF THE INVENTION

A device for imaging scenes with a very large range of intensity comprising a first polarizer, a second polarizer, a primary lens, an attenuating mask, and a imaging device. The first polarizer polarizes light in a first polarization direction. The second polarizer polarizes light in a second polarization direction. Along an optical axis, the second polarizer is positioned between the first polarizer and the primary lens, the attenuating mask is positioned between the primary lens and the imaging device. The first polarizer, the second polarizer, the primary lens, the attenuating mask, and the imaging device are optically connected passing at least some light from the scenes through the first polarizer, the second polarizer, the primary lens, and the attenuating mask to the imaging device. The angle between the first polarization direction and the second polarization direction is adjustable. In one embodiment, one or more additional filters are added along the optical axis path for additional attenuation.

DETAILED DESCRIPTION OF THE INVENTION

A device for imaging scenes with a very large range of intensity comprising a first polarizer, a second polarizer, a primary lens, an attenuating mask, and a imaging device. The first polarizer polarizes light in a first polarization direction. The second polarizer polarizes light in a second polarization direction. Along an optical axis, the second polarizer is positioned between the first polarizer and the primary lens, the attenuating mask is positioned between the primary lens and the imaging device. The first polarizer, the second polarizer, the primary lens, the attenuating mask, and the imaging device are optically connected passing at least some light from the scenes through the first polarizer, the second polarizer, the primary lens, and the attenuating mask to the imaging device. The angle between the first polarization direction and the second polarization direction is adjustable. In one embodiment, one or more additional filters are added along the optical axis path for additional attenuation.

First Polarizer and Second Polarizer

The first polarizer polarizes light into the first polarization direction. The second polarizer polarizes light into the second polarization direction. The first polarizer and the second polarizer are optically connected so that at least some light from the scenes to be imaged by the imaging device passes through the first polarizer and the second polarizer along an optical axis. The first polarizer is preferably a linear polarizer selected from a group including, but is not limited to, wire-grid polarizers, Polaroid films, elongated silver nanoparticle polarizers, quartz crystal polarizers, Glan-type polarizers, other absorptive, beam-splitting, birefringent or thin-film polarizers, or the combination thereof. The second polarizer is preferably a linear polarizer selected from a group including, but is not limited to, wire-grid polarizers, Polaroid films, elongated silver nanoparticle polarizers, quartz crystal polarizers, Glan-type polarizers, other absorptive, beam-splitting, birefringent or thin-film polarizers, or the combination thereof.

An alternative embodiment of the first polarizer is a combination of a variable wave retarder and a linear polarizer selected from a group enumerated above. An alternative embodiment of the second polarizer is a combination of a variable wave retarder and a linear polarizer selected from a group enumerated above.

Depending on the angle between the first polarization direction and the second polarization direction, light going through the first polarizer and the second polarizer is attenuated. The attenuation of light passing through the first polarizer and the second polarizer is minimized when the first polarization direction is parallel with the second polarization direction. The attenuation of light passing through the first polarizer and the second polarizer is maximized when the first polarization direction is perpendicular to the second polarization direction. The attenuation of light is variable from the minimum to the maximum attenuation as the first polarization direction and the second polarization direction change from being parallel to perpendicular to each other. Preferably, a linear polarizer is used for the first polarizer, and another linear polarizer is used for the second polarizer, as they will provide a simpler attenuating adjustment than other types (e.g. using a variable wave retarder).

One preferred embodiment of the first polarizer is a silver impregnated glass polarizer, and one preferred embodiment of the second polarizer is a silver impregnated glass polarizer, where the surface of the first polarizer and the surface of the second polarizer are perpendicular to the optical axis.

Preferably, the angle between the first polarization direction and the second polarization direction is adjustable either manually or using a motorized or electronic means. One embodiment of manually adjusting the angle between the first polarization direction and the second polarization direction is manually rotating the first polarizer, the second polarizer, or the combination thereof around the optical axis, where a rotation stage houses the first polarizer and another rotation stage houses the second polarizer.

Figure 4A:
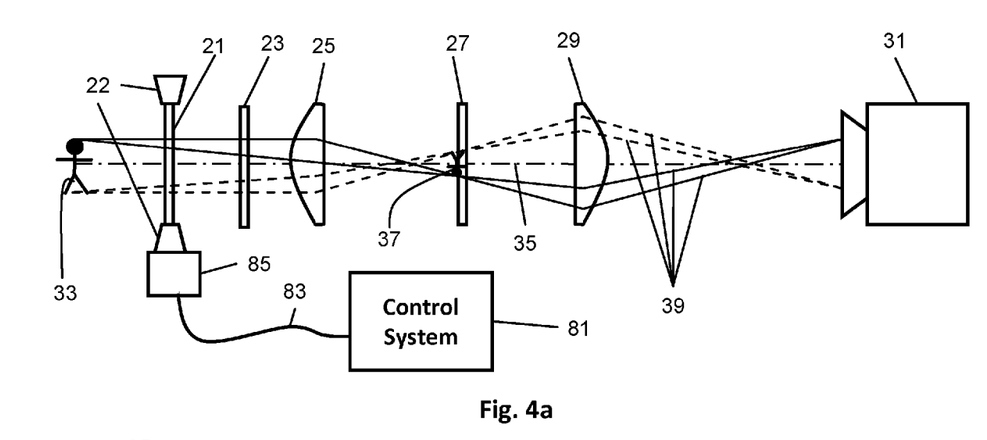
FIG. 4a depicts an embodiment of a device for imaging scenes with very large ranges of intensity in which a motorized means rotates the first polarizer.
Figure 7:
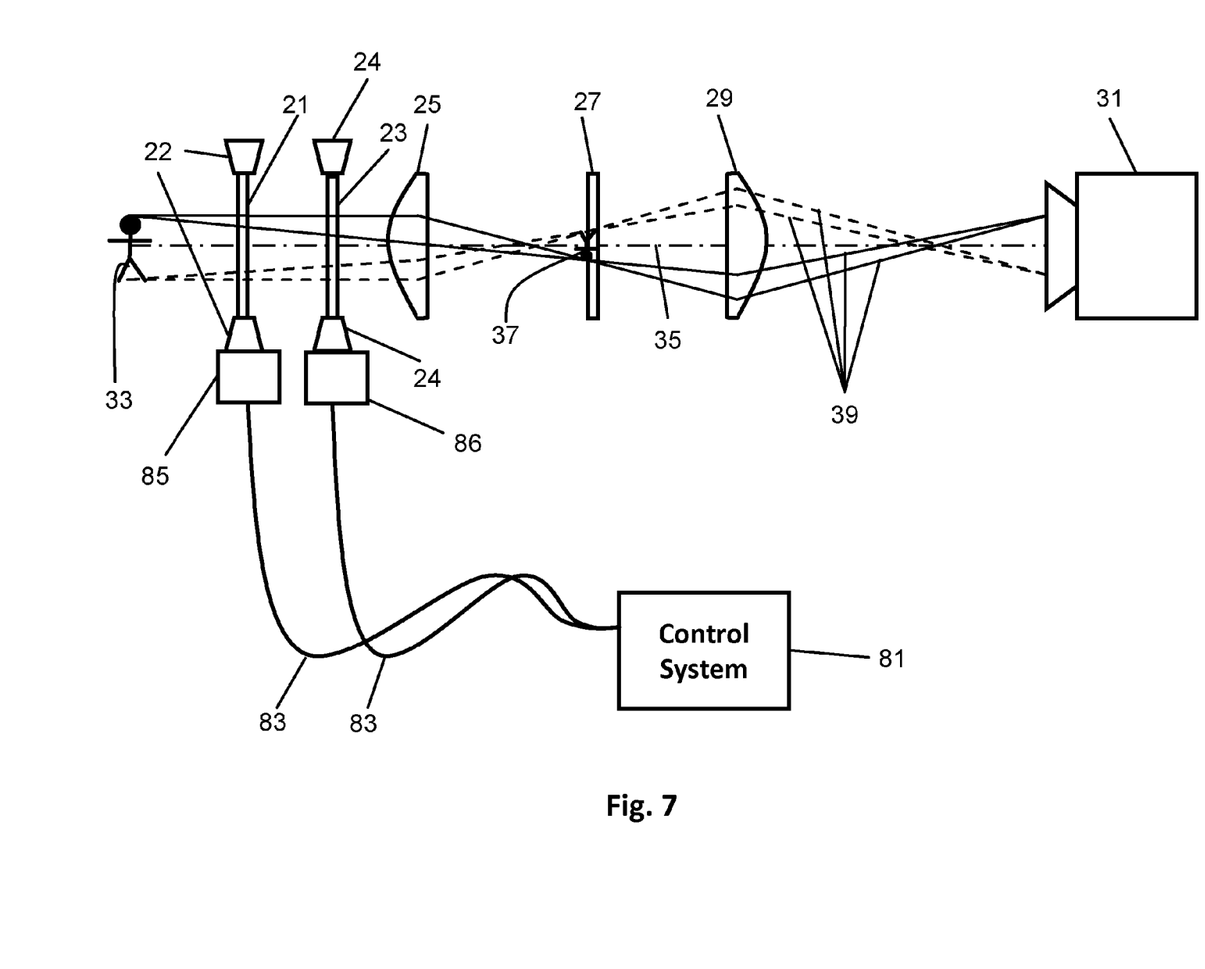
FIG. 7 depicts a preferred embodiment of a device for imaging scenes with very large ranges of intensity in which the first polarization direction and the second polarization direction are changed via a motorized means.

One embodiment of using a motorized means for adjusting the angle between the first polarization direction and the second polarization direction uses a motorized gear box attached to the first polarizer, the second polarizer, or the combination thereof, whereby the motorized gear box rotates the first polarizer, the second polarizer, or the combination thereof around the optical axis. Exemplary embodiments are shown in FIG. 4a and FIG. 7.

One embodiment of using an electronic means for adjusting the angle between the first polarization direction and the second polarization direction uses a combination of a linear polarizer and a variable liquid crystal retarder (VLCR) as the first polarizer, and a linear polarizer as the second polarizer. In this embodiment, light passes through the linear polarizer of the first polarizer, the VLCR, and the second polarizer in the stated order, where the fast axis of the FLCR is at about 45 degrees with the polarization direction of the linear polarizer of the first polarizer. The VLCR changes the retardation between zero and half-wave depending on the voltage applied to the VLCR, thereby varying the first polarization direction by up to 90 degrees. See FIG. 4b for an exemplary embodiment.

Primary Lens

The primary lens focuses light from the scenes along the optical axis onto the attenuating mask. Preferably, the primary lens has adequate image forming ability and freedom from aberrations to match the image quality requirements of the final application. Furthermore, the primary lens should be free of birefringence effects or other defects that could alter the polarization of the light passing through them.

Attenuating Mask

The attenuating mask is positioned along the optical axis and in or substantially near where light from the scenes to be imaged by the imaging device is focused to an image plane by the primary lens. The attenuating mask attenuates light from a part of the scenes, but not the entire area of the scenes, while transmitting light from the other areas of the scenes without substantial attenuation. One embodiment of the attenuating mask is a static, i.e. non-dynamic attenuating mask having an attenuating pattern fixed on the mask. Preferably, the size and shape of the mask is designed to match the size and shape of the image of the area of maximum intensity. See FIG. 3a or FIG. 3b for two examples of embodiments of static attenuating masks.

An alternative embodiment of the attenuating mask is a dynamically attenuating mask including a pixelated liquid crystal light valve (LCLV) and a control system, where the control system dynamically changes the transmission through each pixel of the LCLV, thereby changing the area and the level of attenuation. See FIG. 5 for an exemplary embodiment.

Another embodiment of the attenuating mask is a dynamically attenuating mask including a micro-electromechanical system (MEMS) mirror device and a control system, where the MEMS mirror device selectively reduces the amount of light from the bright areas of the scenes by deflecting such light away from the angle going into the imaging device. See FIG. 6 for an exemplary embodiment.

In yet another embodiment, the attenuating mask is a polarizer. In this embodiment, the first polarizer and the second polarizer are preferably rotatable both relative to each other and as a pair relative to the mask polarization angle allowing the polarization outputted at the second polarizer to be adjusted without changing the global attenuation (from the first polarizer and the second polarizer). In this embodiment, the attenuating mask polarizes light from part of the scenes, therefore attenuating light from only a part of the scene. This is contrary to the first polarizer and second polarizer which both polarizes the entire scene, and therefore globally attenuate (attenuate the entire scene.) See FIG. 7 for an exemplary embodiment.

Imaging Device

Light passing through the first polarizer, the second polarizer, the primary lens, and the attenuating mask is preferably focused by the secondary lens onto an active area of the imaging device, whereby the information regarding the intensity of the light within the active area of the primary device is obtained. Preferably, the imaging device is a film camera, charge-injection device (CID), charge-coupled device (CCD), complementary metal oxide silicon (CMOS) imaging device, or other imaging device. In one embodiment, the imaging device captures light outside the visible spectrum (i.e. in the IR or UV, etc.).

In a preferred embodiment, the imaging device obtains light intensity information on a pixel-by-pixel basis (e.g. CID, CCD, and CMOS imaging device) and sends the light intensity information to the control system for dynamically attenuating the light from the scenes to the imaging device. The CID is a preferred embodiment of the imaging device when in a radioactive environment, as it is resistant to interference from radioactive radiation.

Additional Filters

One or more additional filters (e.g. spectral or neutral density filters) may be added along the optical axis. Preferably, any additional filters are designed to be moveable in or out of the optical axis allowing viewing of the scenes with or without the one or more additional filters.

In one embodiment, fixed, global neutral density filters or spectral filters that reject light intensities or spectral content outside the limits of performance of other optical components are positioned along the optical axis, preferably before the first polarizer. As many of the components, including the first polarizer and second polarizer may have limited spectral ranges, it may be necessary to introduce a spectral bandwidth filter to prevent out of spec light from leaking through the other components. Such leakage would degrade image contrast and perhaps resolution, as well.

In another embodiment, neutral density filters are used to reduce the maximum light intensity (after being attenuated by the system) to a level suitable for the imaging device. This embodiment is preferable for scenes having extreme light intensity either sustained or temporary.

FIG. 1a

Figure 1A:
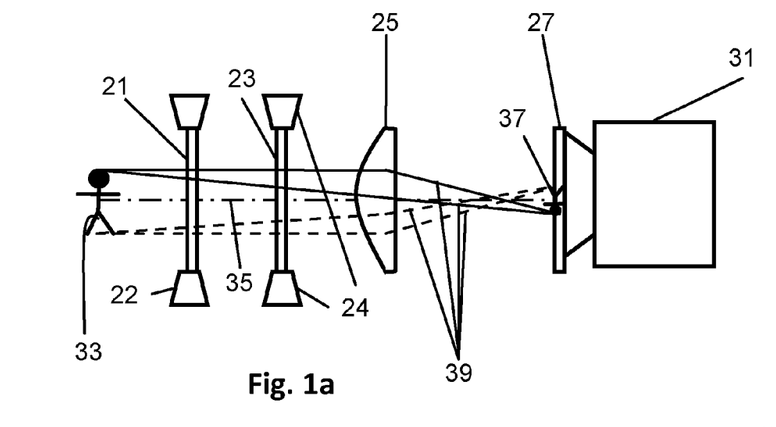
FIG. 1a depicts one embodiment of a device for imaging scenes with very large ranges of intensity.

FIG. 1a depicts one embodiment of a device for imaging scenes with very large ranges of intensity. In this embodiment, light from scenes 33 passes through a first polarizer 21, a second polarizer 23, a primary lens 25, and an attenuating mask 27 to an imaging device 31 along an optical axis 35. In the embodiment shown in FIG. 1a, the first polarizer 21, housed in a first rotatable polarizer holder 22, rotates about the optical axis 35, whereby the angle between the first polarization direction and the second polarization direction is manually adjustable. Likewise, in the embodiment shown in FIG. 1a, the second polarizer 23, housed in a second rotatable polarizer holder 24, rotates about the optical axis 35, whereby the angle between the first polarization direction and the second polarization direction is manually adjustable. Preferably, the attenuating mask 27 is positioned adjacent to the imaging device 31, whereby the image formed on the active area of the imaging device 31 is in focus.

Although, the embodiment shown in FIG. 1 has a first rotatable polarizer holder 22 and a second rotatable polarizer holder 24. either one of the first rotatable polarizer holder 22 or the second rotatable polarizer holder 24, may be omitted, since the rotation of only one polarizer will adjust the angle between the first polarization direction and the second polarization direction, thereby attenuating light.

Exemplary light paths 39 from the scene 33 to a imaging device 31 are shown. The attenuating mask 27 is positioned along the optical axis 35 and in or substantially near an aerial image 37 of the scene 33. The aerial image 37 is the focused image of light from the scene 33 after the light passes through the first polarizer 21, the second polarizer 23, and the primary lens 25. The attenuating mask 27 attenuates light from a partial area of the scene 33 coming through the first polarizer 21, the second polarizer 23, and the primary lens 25, thereby keeping the entire area of the scene 33 within the dynamic range for light intensity of the imaging device 31. The partial area of the scene 33 is preferably a bright area of the scene 33, whereby the light intensity focused on the imaging device 31 saturates all pixels of the imaging device 31 in the area, and the mask is designed to match the bright area.

FIG. 1b

Figure 1B:
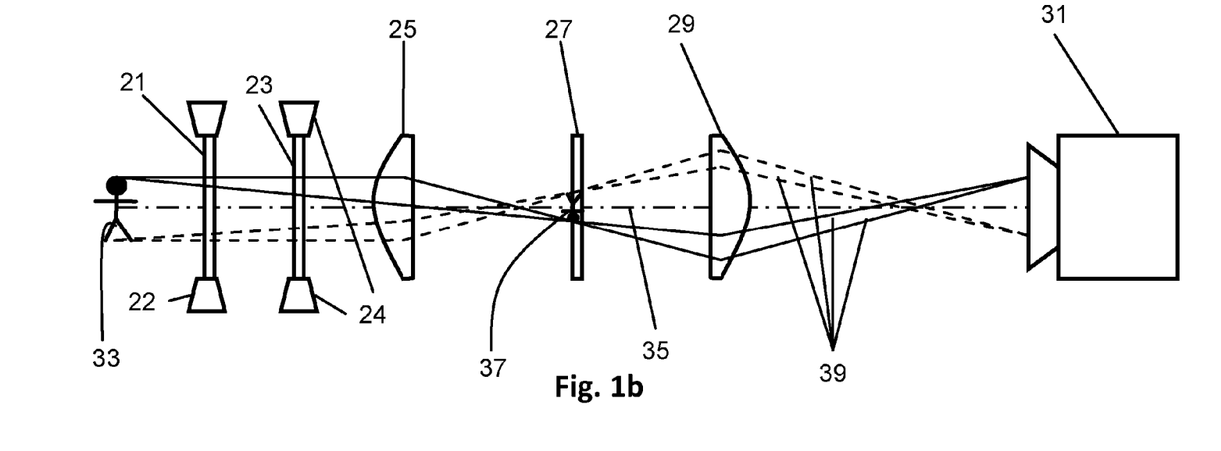
FIG. 1b depicts one embodiment of a device for imaging scenes with very large ranges of intensity having a secondary lens.

FIG. 1b depicts one embodiment of a device for imaging scenes with very large ranges of intensity having a secondary lens 29. In this embodiment, light from scenes 33 pass through a first polarizer 21, a second polarizer 23, a primary lens 25, an attenuating mask 27, a secondary lens 29 to an imaging device 31 along an optical axis 35. This embodiment has the same first polarizer 21, second polarizer 23, primary lens 25, an attenuating mask 27 and imaging device 31 as described in the embodiments of FIG. 1a.

The secondary lens 29 collects the transmitted light through the attenuating mask and focuses the scenes onto the imaging device. Preferably, both the primary lens 25 and the secondary lens 29 have adequate image forming ability and freedom from aberrations to match the image quality requirements of the final application. Furthermore, the primary lens 25 and the secondary lens 29 are preferably free of birefringence effects or other defects that could alter the polarization of the light passing through them.

FIG. 2a

Figure 2A:
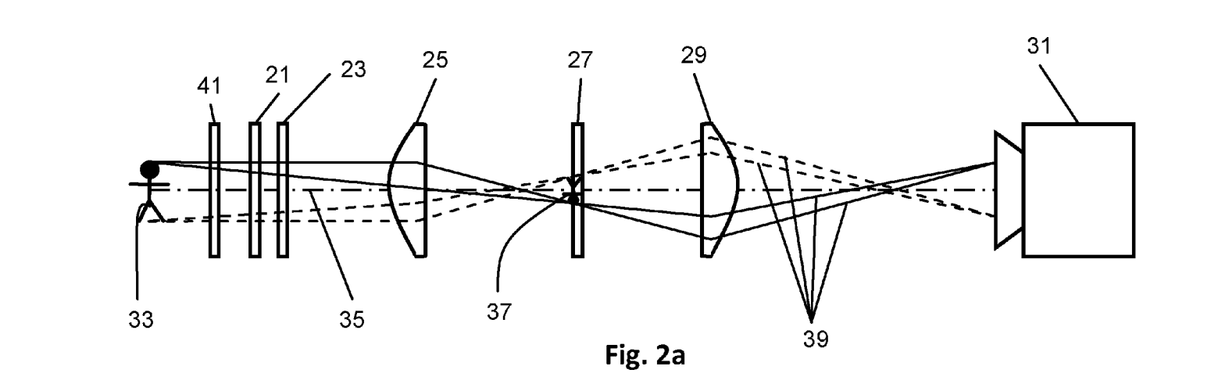
FIG. 2a depicts one embodiment of a device for imaging scenes with very large ranges of intensity having a hot mirror with 0° angle of incidence.

FIG. 2a depicts one embodiment of a device for imaging scenes with very large ranges of intensity having a hot mirror 41 along the optical axis 35 before light from the scenes passes to the first polarizer 21. In this embodiment, light from scenes 33 pass through the hot mirror 41, a first polarizer 21, a second polarizer 23, a primary lens 25, an attenuating mask 27, and a secondary lens 29 to an imaging device 31 along an optical axis 35. This embodiment has the same first polarizer 21, second polarizer 23, primary lens 25, an attenuating mask 27, secondary lens 29, and imaging device 31 as described in the embodiments.

The hot mirror 41 substantially reflects heat (e.g. infrared light) or other unwanted radiation from the scenes 33, mostly allowing the transmission of visible light to pass through the first polarizer 21, the second polarizer 23, the primary lens 25, the attenuating mask 27, the secondary lens 29, and the imaging device 31. Preferably, the hot mirror 41 is made of a glass plate, one of whose surface is coated with multiple stacks of layers of thin film. In one embodiment, the index of refraction of the glass plate is 1.52, and each stack of five consists of a 75.3 nm-thick $SiO_2$ layer, a 91.7 nm-thick $TiO_2$ layer, and a 75.3 nm-thick $SiO_2$ layer stacked in the above-mentioned order, where the indices of refraction are 1.46 at 550 nm for $SiO_2$ and 2.4 at 550 nm for $TiO_2$.

FIG. 2b

Figure 2B:
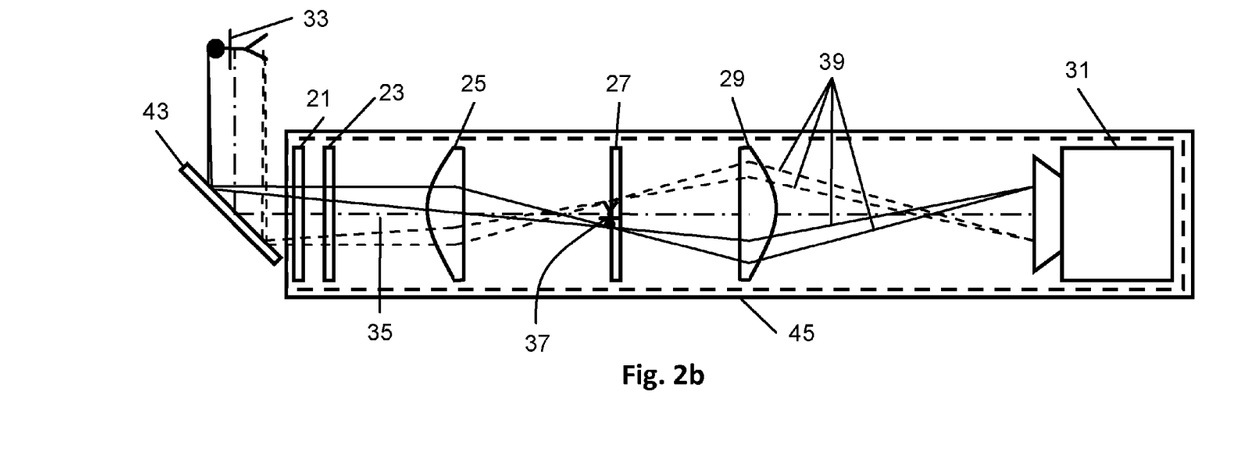
FIG. 2b depicts one embodiment of a device for imaging scenes with very large ranges of intensity having a cold mirror with 45° angle of incidence.

FIG. 2b depicts one embodiment of a device for imaging scenes with very large ranges of intensity having a cold mirror 43. In this embodiment, light from scenes 33 is reflected off the cold mirror 41 and passes through a first polarizer 21, a second polarizer 23, a primary lens 25, an attenuating mask 27, and a secondary lens 29 to an imaging device 31 along an optical axis 35. A radiation shield preferably surrounds the first polarizer 21, second polarizer 23, primary lens 25, attenuating mask 27, secondary lens 29 and imaging device 31. The radiation shield is made of a material which substantially absorbs or reflects radiation.

This embodiment has the same first polarizer 21, second polarizer 23, primary lens 25, an attenuating mask 27, secondary lens 29, and imaging device 31 as described in the above discussed embodiments. In this embodiment, substantial amount of the heat (e.g. infrared light) from the scenes 33 is transmitted through the cold mirror 43, while the cold mirror 43 mostly reflects visible light to the first polarizer 21, the second polarizer 23, the primary lens 25, the attenuating mask 27, the secondary lens 29, and the imaging device 31. This arrangement provides a means of rejecting excess Infrared radiation from the scenes before it enters the optical system and potentially damages the optical components. Alternatively, one could choose a mirror designed to selectively pass or reflect one spectral region into the primary system, while sending unwanted portions of the spectrum (i.e. gamma or x-rays) to a dump.

Preferably, the cold mirror 43 is made of a glass plate, one of whose surfaces is coated with multiple stacks of layers of thin film. In one embodiment, the index of refraction of the glass plate is 1.52, and four different set of stacks are coated on the glass plate. In a preferred embodiment, the first set of stacks, closest to the glass plate, consists of five stacks of a 34.4 nm-thick $TiO_2$ layer, a 113.0 nm-thick $SiO_2$ layer, and a 34.4 nm-thick $TiO_2$ layer stacked in the above-mentioned order; the second set of stacks consists of five stacks of a 28.6 nm-thick $TiO_2$ layer, a 94.2 nm-thick $SiO_2$ layer, and a 28.6 nm-thick $TiO_2$ layer stacked in the above-mentioned order; the third set of stacks consists of five stacks of a 22.9 nm-thick $TiO_2$ layer, a 75.3 nm-thick $SiO_2$ layer, and a 22.9 nm-thick $TiO_2$ layer stacked in the above-mentioned order; and the last set of stacks consists of a 188.4 nm-thick $SiO_2$ layer, where the indices of refraction are 1.46 at 550 nm for $SiO_2$ and 2.4 at 550 nm for $TiO_2$.

Preferably, for imaging welding scenes involving high power illumination on the optics and the imaging device 31, the hot mirror 41, the cold mirror 43 or a combination thereof is positioned between the welding or other high temperature scenes and the first polarizer 21, thereby reducing the heat load on the first polarizer 21, the second polarizer 23, the primary lens 25, the attenuating mask 27, the secondary lens 29, and the imaging device 31.

Preferably, for imaging scenes 33 in highly radioactive environments, the cold mirror 43 is used and a radiation shield 45 covers the first polarizer 21, the second polarizer 23, the primary lens 25, the attenuating mask 27, the secondary lens 29, and the imaging device 31 from outside radiation.

Figure 3A:
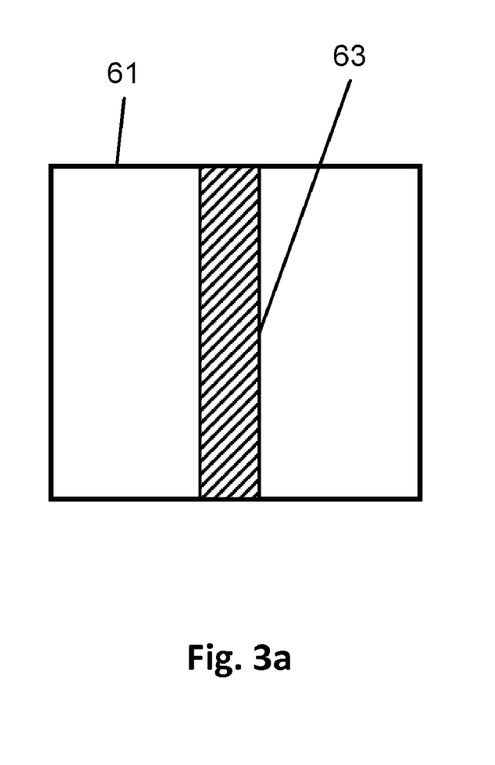
FIG. 3a depicts one embodiment of a static attenuating mask having a vertical attenuating strip.
Figure 3B:
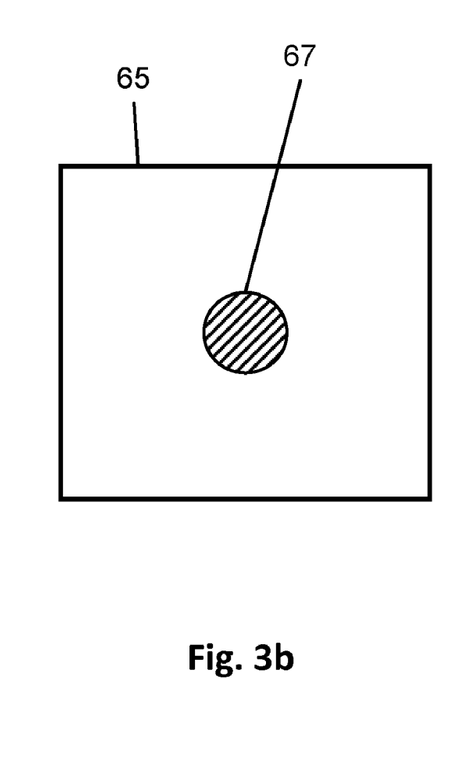
FIG. 3b depicts one embodiment of a static attenuating mask having a circular attenuating area at the center of the attenuating mask.

FIG. 3a and FIG. 3b

FIG. 3a and FIG. 3b depict embodiments of a static attenuating mask 27. FIG. 3a shows one embodiment of a static attenuating mask 61 of which a vertical area 63 at the center is attenuating, while the rest of the static attenuating mask 61 is substantially transparent, preferably attenuating light by less than 10%. One embodiment of the static attenuating mask 61 is a glass plate with a thin film coating only on the center strip of the glass plate, wherein a thin film coating is preferably formed of copper and nickel alloy and is about 100 nm thick.

FIG. 3b shows a static attenuating mask 65 of which a circular area 67 at the center is attenuating, while the rest of the attenuating mask 65 is substantially transparent. One preferred embodiment of the static attenuating mask 65 is a glass plate with a thin film coating only on the circular area at the center of the glass plate, wherein a thin film coating is preferably formed of copper and nickel alloy and is about 100 nm thick.

FIG. 4a

FIG. 4a depicts one embodiment of a device for imaging scenes with very large ranges of intensity in which a motorized means changes the first polarization direction. In this embodiment, light from scenes 33 passes through a first polarizer 21, a second polarizer 23, a primary lens 25, an attenuating mask 27, and a secondary lens 29 to an imaging device 31 along an optical axis 35. This embodiment has the same first polarizer 21, second polarizer 23, primary lens 25, an attenuating mask 27, secondary lens 29, and imaging device 31 as described in the above discussed embodiments. In this embodiment, a first rotatable polarizer holder 22 houses the first polarizer 21. In this embodiment, a first motorized means comprises a motor and gear set 85 attached to the first rotatable polarizer holder 22. The control system 81 is electrically connected via one or more wires 83 to the first motor and gear set 85.

Preferably, the first motor and gear set 85 has a motor and two or more gears which transfer force from the motor to the first rotatable polarizer holder 22 for the first polarizer 21. In one embodiment, the motor in the first motor and gear set 85 is a stepping motor, where the control system 81 sends pulses to the motor in the first motor and gear set 85, thereby controlling the rotation of the first polarizer 21 about the optical axis 35.

In an alternative embodiment, the motor in the first motor and gear set 85 is a DC motor, where the control system 81 sends DC voltages to the motor in the first motor and gear set 85, thereby controlling the rotation of the first polarizer 21 about the optical axis 35. Preferably, in the first motor and gear set 85, a worm gear is attached to the motor's rod, and the worm gear is meshed with a wheel gear attached to the first rotatable polarizer holder 22 around the aperture for the first polarizer 21.

The control system 81 sends electrical pulses or applies DC voltages to the first motor in the motor and gear set 85. One embodiment of the control system 81 has a microcontroller, a central processing unit (CPU), an application-specific integrated circuit (ASIC), a digital-to-analog converter (DAC), a memory, an input device such as a keyboard, a motor driver, or a combination thereof. In one embodiment, the control system 81 receives a keyboard input specifying the direction and the amount of angle by which the first rotatable polarizer holder 22 will be turned. The CPU in the control system 81 processes the input data to calculate the number of pulses to give to the stepping motor in the first motor and gear set 85 or the voltage and time duration to give to the DC motor in the first motor and gear set 85. The CPU then sends the processed information to the DAC. The DAC converts digital signals into analog voltages to the motor driver, which drives the motor in the first motor and gear set 85 connected with the control system 81 via the one or ore wires 83. The CPU might adjust the angle in response to average brightness signals from the imaging device so as to reduce the number of saturated pixels to a minimum. Alternatively, the angle could be adjusted manually using a joystick or other input device.

One alternative embodiment of the control system 81 for driving a DC motor is a regulated DC power supply capable of variable voltage output between 0V and 5V. Still another embodiment of the control system 81 for driving a stepping motor uses a stepping motor controller which preferably drives a stepping motor. In this embodiment, according to the TTL input signals, the stepper motor controller drives the stepping motor in clockwise or counterclockwise direction.

The one or more wires 83 are one or more electrically conductive conductors which electrically connect the various components in the system. In one embodiment, the one or more wires 83 are a pair of electrically conductive connectors, which connects the control system 81 to the motor in the first motor and gear set 85, where the motor is a DC motor. In another embodiment, the one or more wires 83 are a bundle of four or more electrically conductive connectors, which connects the control system 81 to the first motor and gear set 85, where the motor is a stepping motor.

FIG. 4b

Figure 4B:
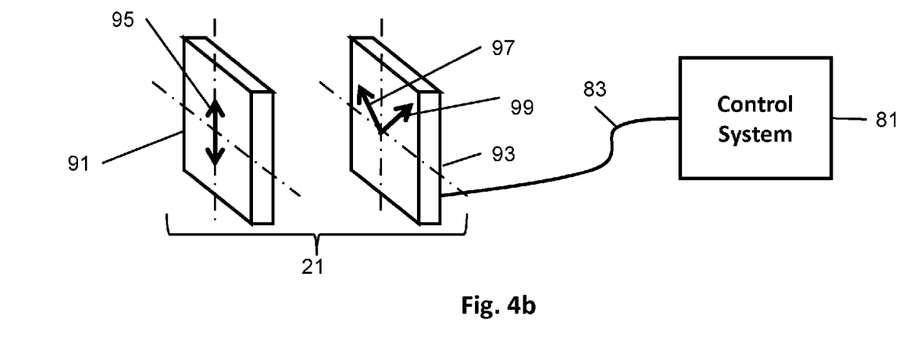
FIG. 4b depicts an embodiment of a device for imaging scenes with very large ranges of intensity in which an electronic means changes the first polarization direction.

FIG. 4b depicts an embodiment of an electronic means for changing the first polarization direction. In a preferred embodiment of the electronic means, the first polarizer 21 comprises a first linear polarizer 91 and a variable wave retarder 93, preferably a variable liquid crystal retarder (VLCR), whose fast axis 97 and slow axis 99 are at 45° with the first linear polarization 95 of the first linear polarizer 91. The variable wave retarder 93 changes the phase difference between light having the polarization direction along the fast axis 97 and light having the polarization direction along the slow axis 99 from zero to a half-wave according to an applied voltage from the control system 81.

In this embodiment, light passing through the first linear polarizer 91 has the first linear polarization 95. When the variable wave retarder 93 changes the phase difference between the fast axis 97 and the slow axis 99 from zero to a half-wave according to an applied voltage from the control system 81 connected via the one or more wires 83, the polarization of the light is further rotated by up to 90° as it passes through the variable wave retarder 93, thereby resulting in the change in the first polarization direction by up to 90°.

In one embodiment of FIG. 4b, the control system 81 is a regulated DC power supply capable of variable voltage output between 0V and 10V, controllable with a potentiometer and an on/off switch. Preferably, the control system 81 is a microcontroller or application-specific integrated circuit capable of (or connected to an integrated circuit having a means for) producing a DC signal.

The one or more wires 83 are one or more electrically conductive conductors which electrically connect the various components in the system. One embodiment of the one or more wires 83 is a pair of electrically conductive connectors, which connect the control system 81 to the VLCR 93.

FIG. 5

Figure 5:
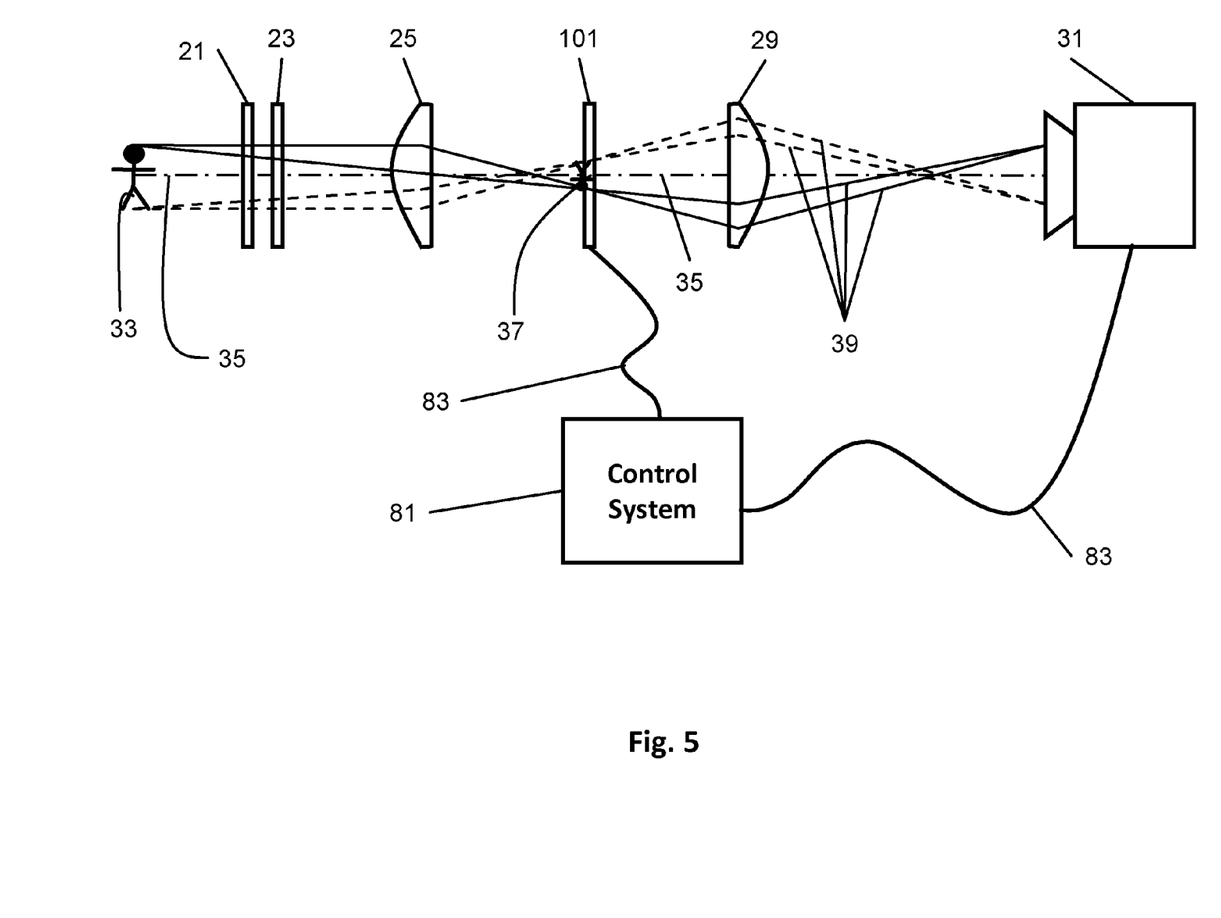
FIG. 5 depicts one embodiment of a device for imaging scenes with very large ranges of intensity having a dynamically adjusted spatial light modulator as the attenuating mask.

FIG. 5 depicts one embodiment of a device for imaging scenes with very large ranges of intensity having a dynamically adjusted spatial light modulator as the attenuating mask.

In this embodiment, light from scenes 33 passes through a first polarizer 21, a second polarizer 23, a primary lens 25, a dynamically adjusted spatial light modulator 101, and a secondary lens 29 to an imaging device 31 along an optical axis 35. This embodiment has the same first polarizer 21, second polarizer 23, primary lens 25, an attenuating mask 27 and imaging device 31 as described in the above discussed embodiments.

Preferably, the dynamically adjusted spatial light modulator 101 is a pixelated liquid crystal light valve (LCLV) or a spatial light modulator (SLM). A control system 81 is connected to the dynamically adjusted spatial light modulator 101 via a one or more wires 83 and to the imaging device 31. The one or more wires 83 are one or more electrically conductive conductors. One exemplary embodiment of the dynamically adjusted spatial light modulator 101 is a liquid crystal display panel sold by Micron Technology under the trademark Displaytech.

In this embodiment, the dynamically adjusted spatial light modulator 101 is positioned at or substantially near the aerial image 37 of the scenes 33 focused by the primary lens 25. The pixel-by-pixel values of light intensity focused onto the imaging device 31 is sent from the imaging device 31 to the control system 81 via one or more wires 83, where an exemplary embodiment of the one or more wires 83 is a DVI-D cable.

In one embodiment, the control system 81 has a microcontroller, a central processing unit (CPU), an application-specific integrated circuit (ASIC), a digital signal processor (DSP), a digital-to-analog converter (DAC), a memory, or a combination thereof. In another embodiment, the control system 81 receives light intensity data from the imaging device 31, processes the light intensity data, and sends controlling signals to the dynamically adjusted spatial light modulator 101 via one or more wires 83, preferably a DVI-I cable.

In a preferable embodiment, the control system 81 is a DSP sold by Texas Instruments under the model number TMS320DM365-300, programmed with development software provided by the manufacturer, to receive light intensity data from the imaging device 31 in digital visual interface (DVI) format, where the pixelated data is encoded using a standard 8b/10b encoding. The DSP then processes the light intensity data by locating the area of saturated pixels by high intensity of light and calculating the amount of attenuation needed for the pixels in the partial area. A DAC in the control system 81 then converts the calculated attenuation for each pixel and selectively sends attenuating signals to the dynamically adjusted spatial light modulator 101 via one or more wires 83, whereby the transmission of light from the scenes 33 through each pixel of the dynamically adjusted spatial light modulator 101 is dynamically controlled to fall within the dynamic range of intensity of the imaging device 31.

FIG. 6

Figure 6:
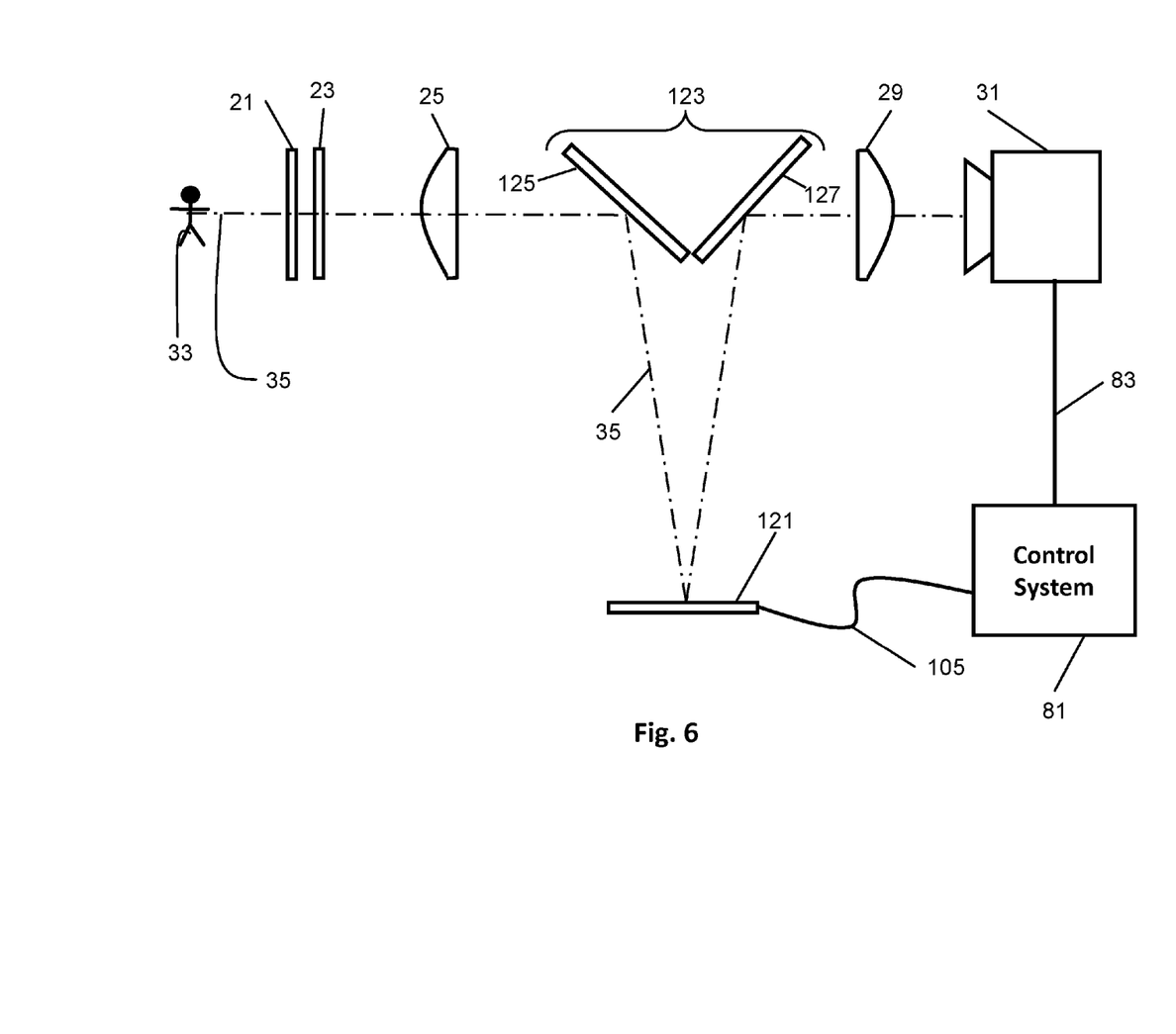
FIG. 6 depicts one embodiment of a device for imaging scenes with very large ranges of intensity having a micro-electromechanical system (MEMS) mirror device as the attenuating mask.

FIG. 6 depicts one embodiment of a device for imaging scenes with very large ranges of intensity wherein the attenuating mask comprises a micro-electromechanical system (MEMS) mirror device 121, a dynamically adjusted spatial light modulator. In this embodiment, light passes from scenes 33, through a first polarizer 21, a second polarizer 23, a primary lens 25, a reflector 123, a MEMS mirror device 121, back to the reflector 123, a secondary lens 29, and an imaging device 103. A control system 81 is connected to the imaging device 31 via one or more wires 83 and the MEMS mirror device 121 via one or more wires 83. The one or more wires 83 are one or more electrically conductive conductors. The reflector 123 is positioned substantially near the aerial image of the scene 33 created by the primary lens 25.

The MEMS mirror device 121 has a plurality of small mirrors, preferably each controlled by a voltage. Each small mirror of the MEMS mirror device 121 can be adjusted whereby the optical path of light passing through each small mirror can be redirected. Therefore, one or more mirrors can be temporarily moved whereby reflected light does not pass along the optical axis to the imaging device 31, thereby reducing its intensity. The MEMS mirror device 121 is preferably a Micromirror, digital micromirror device such as the devices used in DLP video projections, Deformable Mirror Device, or any other light deflection control device. Preferably, each mirror of the MEMS mirror device 121 has a surface area between about 1 to 10,000 microns$^2$.

Although other embodiments having a MEMS mirror device 121 may be used, this embodiment is preferable as the depth of field of the primary lens 25 may be rather small (i.e. the image rapidly blurs with distance from the prime focus), and therefore it may be necessary to introduce the reflector 123. Preferably, the reflector 123 has a first mirror 125 and a second mirror 127. The first mirror 125 directs the optical path 35 to the MEMS device 121 so that the angle of incidence (and of reflection) is nearly perpendicular to the plane of the MEMS device 121. The second mirror 127 reflects the MEMS device 121 reflected beam back onto the original optical path 35. This embodiment should provide superior resolution of the intensity pattern in the scenes 33.

The pixel-by-pixel values of light intensity focused onto the imaging device 31 is sent from the imaging device 31 to the control system 81 via one or more wires 83, where an exemplary embodiment of the one or more wires 83 is a DVI-D cable. An exemplary embodiment of the MEMS mirror device 121 is sold by Texas Instruments under the trademark Digital Micromirror Device (DMD), preferably driven by a digital controller sold by Texas Instruments under the model number DDC4000.

The control system 81 preferably has a microcontroller, a central processing unit (CPU), an application-specific integrated circuit (ASIC), a digital signal processor (DSP), a digital-to-analog converter (DAC), a memory, or a combination thereof. In one embodiment, the control system 81 receives light intensity data from the imaging device 31, processes the light intensity data, and sends controlling signals to the MEMS mirror device 121 via the one or more wires 83, preferably a DVI-I cable.

In a preferred embodiment of the control system 81, DSP sold by Texas Instruments under the model number TMS320DM365-300 is programmed with a development software provided by the manufacturer to receive light intensity data from the digital output port of the imaging device 31 in digital visual interface (DVI) format, where the pixelated data is encoded using a standard 8b/10b encoding. The DSP then processes the light intensity data by locating the area of saturated pixels by high intensity of light and calculating the amount of attenuation needed for the pixels in the partial area. A driver for the MEMS mirror device 121 (e.g. DDC4000) of the control system 81 further converts the calculated attenuation for each pixel and selectively sends attenuating signals to the MEMS mirror device 121 via the one or more wires 83, whereby the pixels in the MEMS mirror device 121 periodically reflect part of the excessively bright away from the second mirror 127 and therefore away from the imaging device 31.

In an alternate embodiment, other reflective dynamically adjusted spatial light modulators may be used in-place of or in addition to the MEMS mirror device 121. For example, a Hammamatsu liquid crystal on Silicon spatial light modulators that operate in a reflective mode may be used in place of the MEMS mirror device 121.

FIG. 7

FIG. 7 depicts a preferred embodiment of a device for imaging scenes with very large ranges of intensity in which the first polarization direction and the second polarization direction are changed via a motorized means. In this embodiment, light from scenes 33 passes through a first polarizer 21, a second polarizer 23, a primary lens 25, an attenuating mask 27, and a secondary lens 29 to an imaging device 31 along an optical axis 35. This embodiment has the same first polarizer 21, second polarizer 23, primary lens 25, an attenuating mask 27 and imaging device 31 as described in the above discussed embodiments. In this embodiment, a first rotatable polarizer holder 22 houses the first polarizer 21 and a second rotatable polarizer holder 24 houses the second polarizer 23.

A first motor and gear set 85 is attached to the first rotatable polarizer holder 22. Likewise, a motorized means comprises a second motor and gear set 86 is attached to the second rotatable polarizer holder 24. The control system 81 is electrically connected via one or more wires 83 to the first motor and gear set 85 and the second motor and gear set 86. The one or more wires 83 are one or more electrically conductive conductors.

Preferably, the attenuating mask 27 uses a third polarizer to polarize light in a third direction, whereby the attenuation of light by the attenuation mask 27 is dependent upon the rotational position of the attenuating mask 27 and the second polarization direction, produced by the second polarizer 23. In this embodiment, both the first motor and gear set 85 and the second motor and gear set 86 are preferably used so that adjustments may be made to the amount of global attenuation performed between the first polarizer 21 and the second polarizer 23 and the attenuation of only a partial are of the scenes 33 between the second polarizer 23 and the attenuating mask 27. In the alternative, either one of the first motor and gear set 85 or the second motor and gear set 86 may be omitted and the attenuation mask 27 may be rotated. As the attenuation mask 27 may have a shape that will change the attenuated area of the scenes 33 upon rotation, it is preferable to rotate both the first polarizer 21 and the second polarizer 23 instead of rotating the attenuating mask 27.

Therefore, one can globally change light passing to the imaging device 31 by changing the angle between the first polarization direction (from the first polarizer 21) and the second polarization direction (from the second polarizer 23). This can be done by rotating either the first polarizer 21 or the second polarizer 23. In the alternative, both the first polarizer 21 and the second polarizer 23 may be rotated in opposite directions as well.

Additionally, one can attenuate a partial area by changing the angle between the second polarization direction (from the second polarization mask 23) and the third polarization direction (from the attenuating mask 27). Preferably, a partial area is attenuated using the attenuation mask 27 (preferably made of a polarizing material) by rotating both the first polarizer 21 and the second polarizer 23 in the same direction. By rotating both first polarization direction (from the first polarizer 21) and the second polarization direction (from the second polarizer 23) in the same direction, the angle between the first polarization direction and the second polarization direction will remain the same and therefore the global attenuation will not be changed. However, the angle between the second polarization direction (from the second polarization mask 23)

and the third polarization direction (from the attenuating mask 27) will be changed thereby changing the amount of attenuation to a partial area of the scene 33 by the attenuating mask 27. In the alternative, the attenuating mask 27 can also be rotated in lieu of or in addition to, however this may alter the shape of the attenuated area of actual attenuating mask 27, which may or may not be desirable depending on the situation.

Each motor and gear set (the first motor and gear set 85 and the second motor and gear set 86) can be any method of rotating the polarizers, for example as discussed above for the first the first motor and gear set 85 in FIG. 4a.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

All publications and patent documents cited in this application are incorporated by reference in their entirety for all purposes to the same extent as if each individual publication or patent document were so individually denoted.

Any element in a claim that does not explicitly state "means for" performing a specified function, or "step for" performing a specific function, is not to be interpreted as a "means" or "step" clause as specified in 35 U.S.C. §112, ¶ 6.

The invention claimed is:

1. A device for imaging scenes with a very large range of intensity comprising:
   a. a first polarizer polarizing light in a first polarization direction;
   b. a second polarizer polarizing light in a second polarization direction;
   c. a primary lens;
   d. an attenuating mask;
   e. a imaging device;
   f. said second polarizer positioned between said first polarizer and said primary lens along an optical axis;
   g. said primary lens positioned between said second polarizer and said attenuating mask along said optical axis;
   h. said attenuating mask positioned between said primary lens and said imaging device along said optical axis;
   i. said first polarizer, said second polarizer, said primary lens, said attenuating mask, and the active area of said imaging device optically connected along said optical axis; and
   j. a means for adjusting the angle between said first polarization direction and said second polarization direction.

2. The device for imaging scenes with a very large range of intensity of claim 1, further comprising:
   a. a secondary lens;
   b. said attenuating mask positioned between said primary lens and said secondary lens along said optical axis; and
   c. said secondary lens positioned between said attenuating mask and said imaging device along said optical axis.

3. The device for imaging scenes with a very large range of intensity of claim 1, whereby said attenuating mask is a static attenuating mask.

4. The device for imaging scenes with a very large range of intensity of claim 1 further comprising a hot mirror, whereby:
   a. said first polarizer is positioned between said hot mirror and said second polarizer along said optical axis; and
   b. said hot mirror and said first polarizer are optically connected.

5. The device for imaging scenes with a very large range of intensity of claim 4, whereby said imaging device is a CID.

6. The device for imaging scenes with a very large range of intensity of claim 1 further comprising a cold mirror, whereby:
   a. said first polarizer is positioned between said cold mirror and said second polarizer along said optical axis; and
   b. said cold mirror and said first polarizer are optically connected.

7. The device for imaging scenes with a very large range of intensity of claim 6, whereby said imaging device is a CID.

8. The device for imaging scenes with a very large range of intensity of claim 1, whereby:
   a. said first polarizer comprises a linear polarizer and a variable liquid crystal retarder (VLCR);
   b. said second polarizer comprises a linear polarizer; and
   c. said means for adjusting the angle between said first polarization direction and said second polarization direction comprises a control system connected to said VLCR and to said imaging device.

9. The device for imaging scenes with a very large range of intensity of claim 1, further comprising:
   a. said attenuating mask comprising a third polarizer polarizing light in a third polarization direction; and
   b. a means for adjusting the angle between said second polarization direction and said third polarization direction.

10. The device for imaging scenes with a very large range of intensity of claim 9 whereby said means for adjusting the angle between said first polarization direction and said second polarization direction and said means for adjusting the angle between said second polarization direction and said third polarization direction comprises:
    a. a means for rotating said first polarizer; and
    b. a means for rotating said second polarizer.

11. The device for imaging scenes with a very large range of intensity of claim 10, whereby:
    a. said attenuating mask comprises a dynamically adjusted spatial light modulator selected from the group consisting of a pixelated liquid crystal light valve (LCLV) and a micro-electromechanical system (MEMS) mirror device;
    b. said dynamically adjusted spatial light modulator connected to a control system; and
    c. said control system connected to said imaging device.

12. The device for imaging scenes with a very large range of intensity of claim 1, whereby:
    a. said attenuating mask comprises a dynamically adjusted spatial light modulator selected from the group consisting of a pixelated liquid crystal light valve (LCLV) and a micro-electromechanical system (MEMS) mirror device;
    b. said dynamically adjusted spatial light modulator connected to a control system; and
    c. said control system connected to said imaging device.

13. The device for imaging scenes with a very large range of intensity of claim 12 further comprising a hot mirror, whereby:
    a. said first polarizer is positioned between said hot mirror and said second polarizer along said optical axis;
    b. said hot mirror has about 0° angle of incidence; and
    c. said hot mirror and said first polarizer are optically connected.

14. The device for imaging scenes with a very large range of intensity of claim 12 further comprising a cold mirror, whereby:
    a. said first polarizer is positioned between said cold mirror and said second polarizer along said optical axis;
    b. said cold mirror has about 45° angle of incidence; and c. said cold mirror and said first polarizer are optically connected.

15. The device for imaging scenes with a very large range of intensity of claim 14, whereby said imaging device is a CID.

16. A device for imaging scenes with a very large range of intensity comprising:
  a. a cold mirror;
  b. a first polarizer comprising a linear polarizer and a variable liquid crystal retarder (VLCR) and polarizing light in a first polarization direction;
  c. a second polarizer polarizing light in a second polarization direction;
  d. a primary lens;
  e. an attenuating mask comprising a third polarizer polarizing light in a third polarization direction
  f. a secondary lens;
  g. a charge-injection device (CID);
  h. said first polarizer positioned between said cold mirror and said second polarizer along an optical axis;
  i. said second polarizer positioned between said first polarizer and said primary lens along said optical axis;
  j. said primary lens positioned between said second polarizer and said attenuating mask along said optical axis;
  k. said attenuating mask positioned between said primary lens and said secondary lens along said optical axis;
  l. said secondary lens positioned between said attenuating mask and said CID along said optical axis;
  m. said first polarizer, said second polarizer, said primary lens, said attenuating mask, said secondary lens and the active area of said CID optically connected along said optical axis;
  n. said second polarizer is a linear polarizer;
  o. a means for rotating said first polarizer;
  p. a means for rotating said second polarizer; and
  q. a control system connected to said VLCR, said CID, said means for rotating said first polarizer and means for rotating said second polarizer.

* * * * *